United States Patent
Zhang

(10) Patent No.: US 11,224,402 B2
(45) Date of Patent: Jan. 18, 2022

(54) FETAL HEART RATE DETECTION METHOD TO DISCRIMINATE FROM OTHER PERIODIC SIGNAL

(71) Applicant: KONINKLIJKE PHILIPS N. V., Eindhoven (NL)

(72) Inventor: Ying Zhang, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 41 days.

(21) Appl. No.: 16/647,316

(22) PCT Filed: Sep. 11, 2018

(86) PCT No.: PCT/EP2018/074404
§ 371 (c)(1),
(2) Date: Mar. 13, 2020

(87) PCT Pub. No.: WO2019/052988
PCT Pub. Date: Mar. 21, 2019

(65) Prior Publication Data
US 2020/0275907 A1    Sep. 3, 2020

(30) Foreign Application Priority Data

Sep. 13, 2017  (WO) ............... PCT/CN2017/101558
Nov. 1, 2017   (EP) ..................... 17199536

(51) Int. Cl.
*A61B 8/08* (2006.01)
*A61B 8/02* (2006.01)

(52) U.S. Cl.
CPC ............ *A61B 8/0866* (2013.01); *A61B 8/02* (2013.01); *A61B 8/488* (2013.01); *A61B 8/5223* (2013.01)

(58) Field of Classification Search
CPC ......... A61B 8/0866; A61B 8/02; A61B 8/488; A61B 8/5223; G16H 50/30
See application file for complete search history.

(56) References Cited

U.S. PATENT DOCUMENTS 6,816,744 B2  11/2004  Garfield et al.
8,064,991 B2  11/2011  Hersh et al.
(Continued)

FOREIGN PATENT DOCUMENTS

EP   3189776 A1     7/2017
RU   2596719 C1     9/2016
WO   2014159348 A1  10/2014

OTHER PUBLICATIONS

Alnuaimi et al., Fetal Cardiac Doppler Signal Processing Techniques: Challenges and Future Research Directions, Frontiers in Bioengineering and Biotechnology, Dec. 22, 2017, vol. 5, Article 82.*

(Continued)

*Primary Examiner* — Bo Joseph Peng

(57) ABSTRACT

A fetal movement detection method (100) includes: identifying pulse packets in a Doppler ultrasound signal, each pulse packet comprising a pulse train of one or more pulses; classifying each of the identified pulse packets as a hiccup or non-hiccup based on at least one characteristic of the identified pulse packets; suppressing the pulse packets of the Doppler ultrasound signal that are classified as a hiccup; and calculating a fetal heart rate from the Doppler ultrasound signal with the pulse packets classified as hiccups suppressed.

13 Claims, 6 Drawing Sheets

(56) References Cited

U.S. PATENT DOCUMENTS

| | | | |
|---|---|---|---|
| 8,088,082 B2 | 1/2012 | Nishihara et al. | |
| 8,764,686 B2 | 7/2014 | Nishihara | |
| 2012/0083699 A1* | 4/2012 | Reuter | A61B 5/4362 600/453 |
| 2012/0253212 A1* | 10/2012 | Maeno | A61B 5/0051 600/508 |

OTHER PUBLICATIONS

Mert et al., A test and simulation device for Doppler-based fetal heart rate monitoring, Turk J Elec Eng & Comp Sci, 2015, 23, 1187-1194, Published Online: Aug. 13, 2013.*

Nishihara et al., Automated Software Analysis of Fetal Movement Recorded during a Pregnant Woman's Sleep at Home, PLoS ONE 10(6): e0130503. doi:10.1371/journal.pone.0130503, Jun. 17, 2015.*

International Search Report and Written Opinion, International Application No. PCT/EP2018/074404, dated Dec. 10, 2018.

Wheeler, T. et al., "Detection of Fetal Movement Using Doppler Ultrasound", vol. 70, No. 2, Aug. 1987.

Popescu, E. A., et al. "Magnetographic assessment of fetal hiccups and their effect on fetal heart rhythm." Physiological measurement 28.6 (2007): 665.

\* cited by examiner

FETAL HEART RATE DETECTION METHOD TO DISCRIMINATE FROM OTHER PERIODIC SIGNAL

This application is the U.S. National Phase application under 35 U.S.C. § 371 of International Application No. PCT/EP2018/074404, filed on 11 Sep. 2018, which claims the benefit of European Application Serial No. 17199536.8, filed 1 Nov. 2017 and International Application No. PCT/CN2017/101558, filed on 13 Sep. 2017. These applications are hereby incorporated by reference herein.

FIELD

The following relates generally to the Doppler ultrasound arts, fetal monitoring arts, fetal heart rate monitoring arts, and related arts.

BACKGROUND

Existing fetal heart rate monitors employ Doppler ultrasound. In this technique, the Doppler ultrasound amplitude versus time is measured. Each heart beat produces a compact pulse train made up of oscillating pulses. After band pass filtering to remove lower Doppler frequency components due to fetal movements, the fetal heart rate is determined as the rate of occurrence of these pulse trains.

However, a hiccup by the fetus can also produce a pulse train similarly to a heart beat. A bout of hiccups can occur which has a relatively consistent rhythm, and which produces pulse trains of higher amplitude than the heart beats. Such a bout of hiccups can thus be easily mistaken as a (quasi-) periodic fetal cardiac pulse, thereby producing an erroneous fetal heart rate measurement.

The following discloses new and improved systems and methods to overcome these problems.

SUMMARY

In one disclosed aspect, a fetal movement detection method includes: identifying pulse packets in a Doppler ultrasound signal, each pulse packet comprising a pulse train of one or more pulses; classifying each of the identified pulse packets as a hiccup or non-hiccup based on at least one characteristic of the identified pulse packets; suppressing the pulse packets of the Doppler ultrasound signal that are classified as a hiccup; and calculating a fetal heart rate from the Doppler ultrasound signal with the pulse packets classified as hiccups suppressed.

In another disclosed aspect, a device is configured to determine a fetal heart rate includes at least one electronic processor programmed to: identify pulse packets in the Doppler ultrasound signal, each pulse packet comprising a pulse train of one or more pulses; classify each of the identified pulse packets as a hiccup or non-hiccup based on at least one characteristic of the identified pulse packets; suppress the pulse packets of the Doppler ultrasound signal classified as hiccups; and calculate a fetal heart rate from the Doppler ultrasound signal with the pulse packets classified as hiccups suppressed.

One advantage resides in more accurately determining a fetal heart rate.

Another advantage resides in distinguishing pulse packets in a Doppler ultrasound signal that are due to a fetal heart beat from pulse packets due to a fetal hiccup and suppressing the latter when computing the fetal heart rate.

Another advantage resides in providing a low cost system to accurately determine fetal heart rate.

Another advantage resides in determining a threshold value effective to distinguish between fetal heart beats and fetal hiccups.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
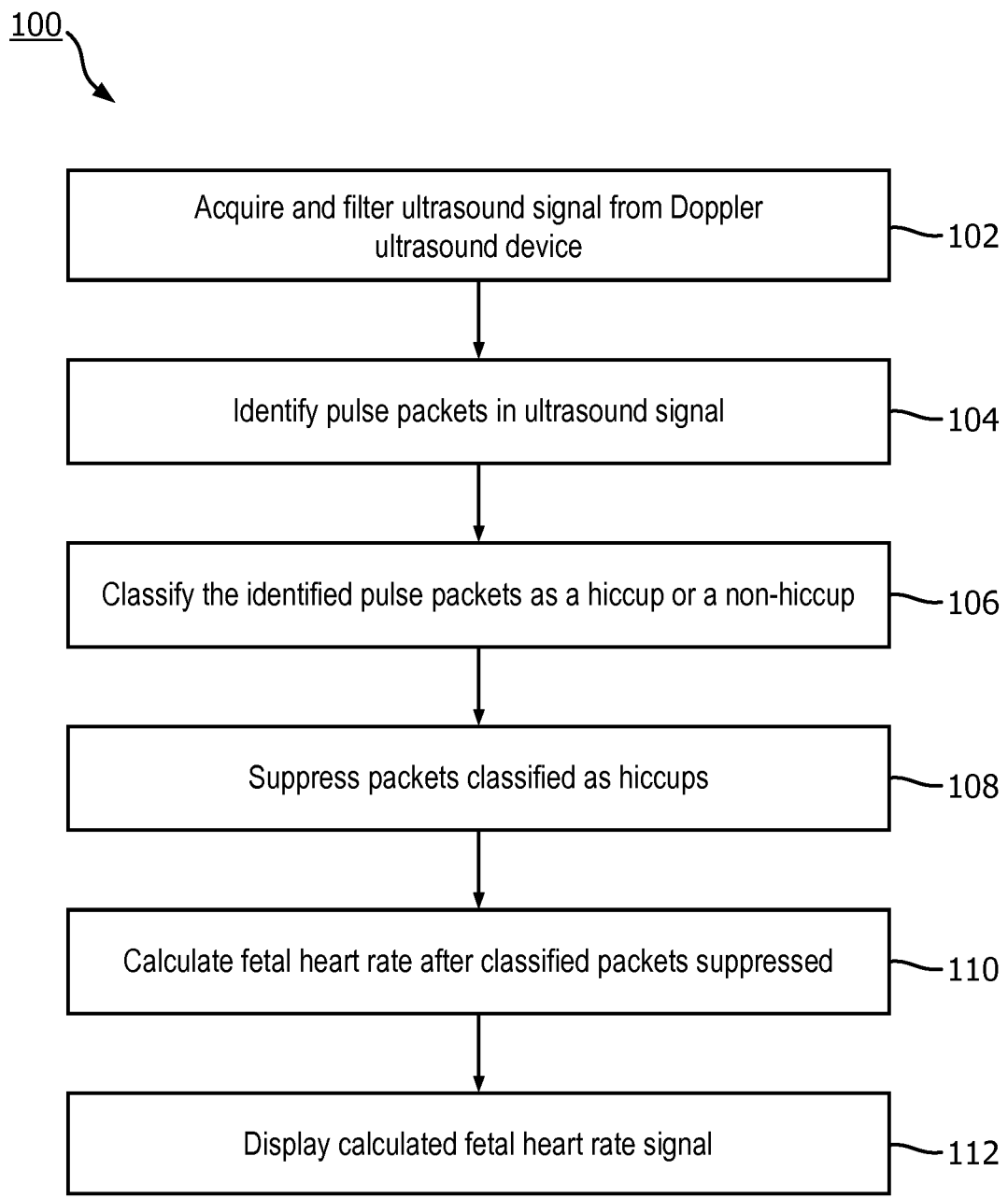
FIG. 1 shows an exemplary flow chart operation a fetal heart rate detection method according to one aspect.

In the Doppler ultrasound signal measured for a fetus, a fetal heart beat appears as a pulse packet made up of a pulse train of relatively short duration, e.g. on the order of 100-200 milliseconds. This pulse train is typically classified or attributed to the systolic stage of the fetal heartbeat, during which the heart contracts to drive blood flow. However, a fetal hiccup can produce a similar pulse packet made up of a pulse train of comparable duration. Moreover, fetal hiccups can occur in a quasi-periodic pattern mimicking a rhythmic fetal pulse. Thus, pulse packets due to fetal hiccups can be erroneously identified as fetal heart beats, which can lead to substantial error in the calculated fetal heart rate, generally reading lower than its actual value due to the "extra" heart beats actually due to hiccups.

The following discloses an improvement in fetal heart rate detection that employs a test to detect whether a pulse packet in the Doppler ultrasound amplitude versus time signal is due to a hiccup—if so, the hiccup pulse packet is suppressed prior to computing the fetal heart rate. One illustrative approach computes the number of pulses (or, equivalently, the number of zero crossings) in the pulse train. As recognized herein, a pulse train due to a heart beat typically has a larger number of pulses than a pulse train due to a hiccup. In clinical data analyses, it was found that a pulse train due to a heart beat typically has about 6 pulses; whereas, a pulse train due to a hiccup typically has about 3 pulses. This result can be generalized to a test in which a pulse count for the pulse packet is computed. The pulse count for a pulse packet identified in the Doppler ultrasound signal may comprise the number of crossings of the time axis (i.e. zero crossing), or may comprise the number of pulse peaks. Any pulse packet whose determined pulse count is at or below a threshold is then attributed to, or classified as, a hiccup or a non-hiccup.

Optionally, machine learning may be used to optimize the typical pulse count of a pulse train due to a heart beat for a particular fetus being monitored. Under the assumption that heart beats statistically dominate over less common hiccups, the approach is to generate a statistical distribution of pulse counts for pulse trains detected for a fetus currently being monitored. When sufficient statistics are gathered, it is expected that this pulse number distribution conforms with a normal distribution. The mean of the distribution is then the typical pulse number for a pulse train produced by a heart beat. The standard deviation (or other distribution "width" metric) provides information on the extent of deviation from this typical pulse number to designate a pulse train as being produced by a hiccup.

Rather than being learned for an individual fetus, the pulse counts for heart beats and for hiccups can be learned for a particular cohort of fetuses, e.g. fetuses in a particular age range, or fetuses with a particular medical condition, or so forth.

When a pulse train is identified as being due to a hiccup, it is removed or suppressed. In an illustrative embodiment, this is done by attenuating the pulse train due to a hiccup by at least 3 dB. In this way, it is made subordinate to pulse trains due to actual heart beats and has negligible effect on the subsequent fetal heart rate calculation.

With reference to FIG. 1, the fetal heart rate detection method 100 is diagrammatically shown as a flowchart. At 102, a Doppler ultrasound signal of a fetus is acquired and filtered the Doppler ultrasound signal with a band pass filter to suppress a fetal movement component of the Doppler ultrasound signal. The band pass filtering operation removes motion data indicative of movement of the fetus not due to thoracic activity.

Figure 2:
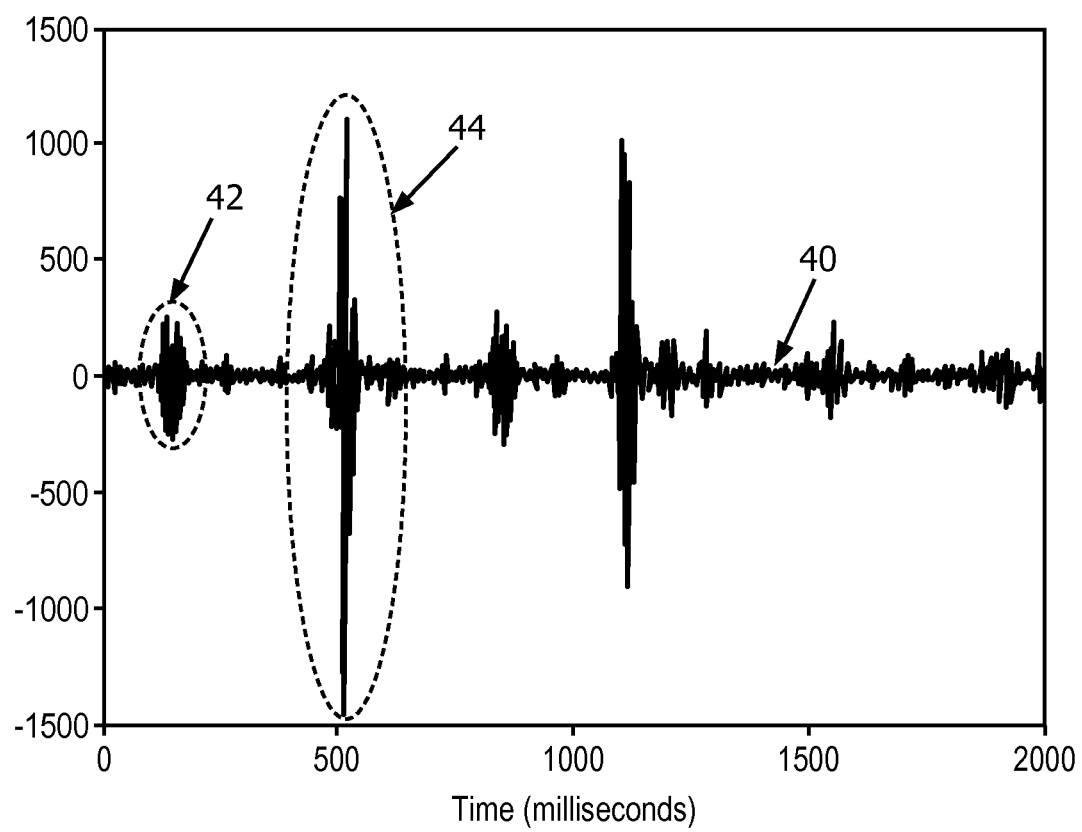
FIG. 2 illustratively shows data acquired by the method of FIG. 1.
Figure 3:
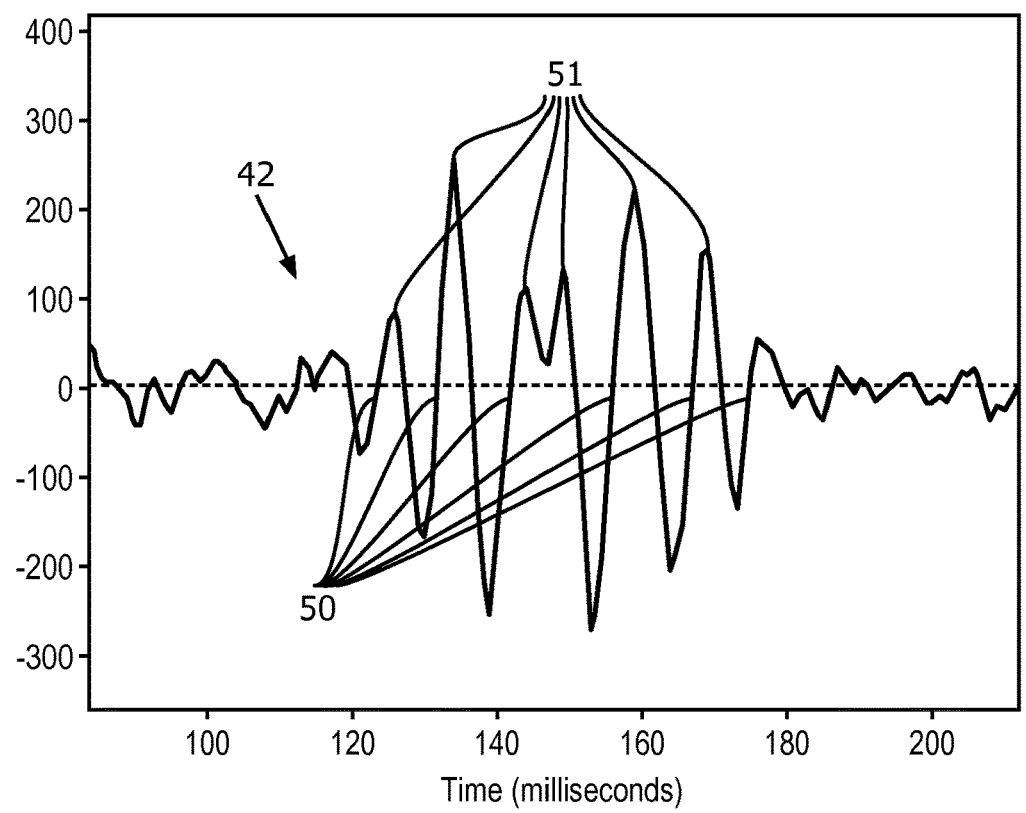
FIG. 3 illustratively shows data acquired by the method of FIG. 1.
Figure 3:
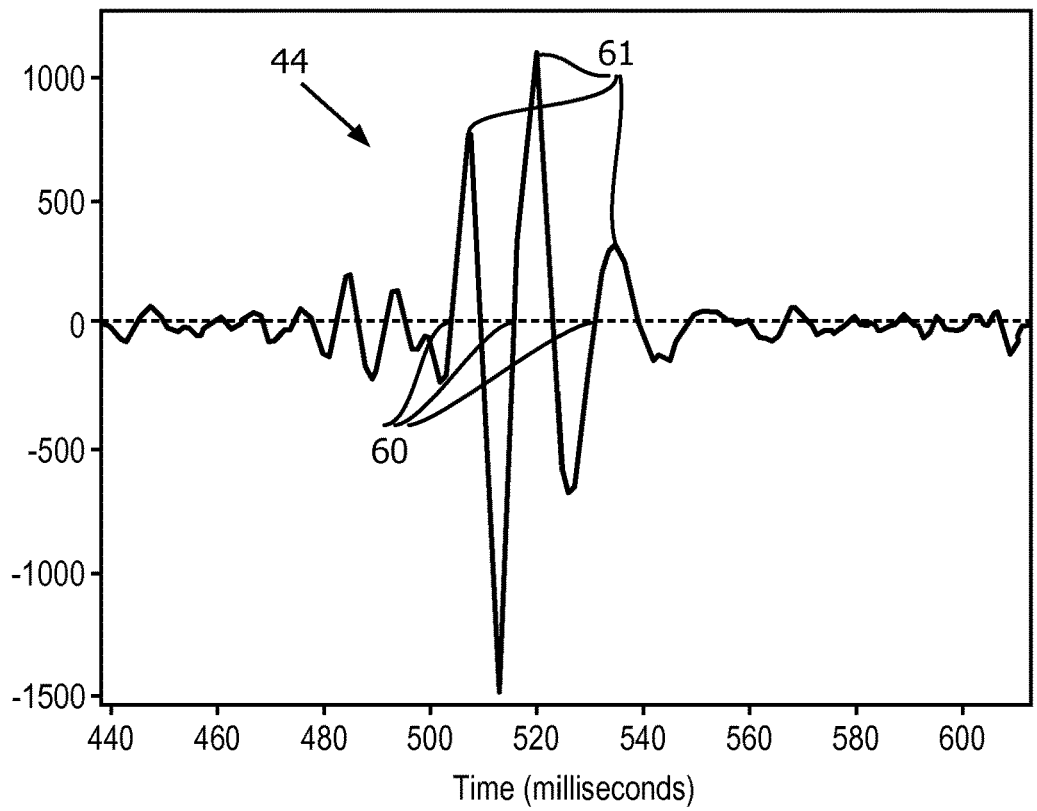

At 104, pulse packets are identified in the Doppler ultrasound signal. Each pulse packet comprises a pulse train of one or more pulses. FIG. 2 illustrates the Doppler ultrasound signal after band pass filtering to suppress fetal movements, where several pulse packets including two labeled as pulse packets 42, 44 are seen. FIG. 3 illustrates expanded views of the illustrative pulse packets 42, 44. Typically, the pulses of the pulse train making up a pulse packet increase rapidly in amplitude from a signal value close to the noise floor at the beginning of the pulse packet to reach a maximum pulse amplitude approximately near the center of the pulse packet, and the pulses then decrease in amplitude back to the noise floor. Furthermore, the pulse packets due to heartbeats (and also due to hiccups) are typically of duration on the order of a few tens of milliseconds to a couple hundred milliseconds or so. The remaining portions of the Doppler ultrasound signal can be discarded.

At 106, each of the identified pulse packets of the Doppler ultrasound signal are classified as a hiccup or a non-hiccup based on at least one characteristic of the identified pulse packets. In some embodiments, the at least one characteristic includes determining a pulse count comprising a number of crossings of the time axis or a number of pulse peaks for each of the pulse packets identified in the Doppler ultrasound signal. Once the number of crossings or peaks is determined for each pulse packet, any pulse packet whose determined pulse count is at or below a threshold is classified as a hiccup, and all other identified pulse packets (e.g., above the threshold) are classified as a non-hiccup. For example, in some performed calibrations it was found that setting the threshold to be three crossings provided effective distinguishing between pulse packets due to hiccups (having three pulses or fewer) and pulse packets due to heartbeats (having four or more pulses).

In other embodiments the at least one characteristic of the identified pulse packets includes a statistical distribution of the pulse counts of the pulse packets identified in the Doppler ultrasound signal is generated. For example, data is collected until the statistical distribution is normalized. The threshold is selected based on the normalized statistical distribution.

Referring back to FIG. 1, at 108, any pulse packets of the Doppler ultrasound signal which are classified as hiccups at 106 are suppressed. In one approach, the pulse packets due to hiccups are suppressed by attenuating the Doppler ultrasound signal with at least 3 dB to suppress the pulse packets classified as hiccups. In another contemplated embodiment, any time segment of the band pass filtered Doppler ultrasound signal that is identified as a pulse packet and classified as a hiccup is replaced by a substitute signal having zero value over the time segment, or having some other suitable value such as a signal equal to the noise floor.

At 110, a fetal heart rate is calculated from the Doppler ultrasound signal with the pulse packets classified as hiccups suppressed (i.e., so that the pulse packets classified as non-hiccups remain). To do so, the fetal heart rate is calculated as a rate of occurrence of the identified pulse packets in the Doppler ultrasound signal with the pulse packets classified as hiccups suppressed.

At 112, the calculated heart rate can be displayed on a display device.

FIGS. 2 and 3 show examples of generated data. FIG. 2 shows a Doppler ultrasound signal 40 after band pass filtering by the band pass filter to remove fetal or maternal motion artifacts. The Doppler ultrasound signal includes a number of pulse packets, including a pulse packet 42 due to a fetal heartbeat and a pulse packet 44 due to a hiccup.

FIG. 3 shows enlarged portions of the pulse packet 42 due to the heart beat and the pulse packet 44 due to the hiccup. As shown in FIG. 3, the pulse packet 42 due to the cardiac pulse includes six crossings the pulse packet 42 due to the cardiac pulse includes six crossings of the zero value of the amplitude axis in which the Doppler ultrasound signal crosses from negative to positive 50 of the zero value of the amplitude axis in which the Doppler ultrasound signal crosses from negative to positive. Viewed alternatively, the pulse packet 42 due to the cardiac pulse includes six pulse peaks 51. These values are higher than the threshold of three crossings determined from clinical data analyses. Therefore, the electronic processor 22 determines that the cardiac pulse 42 is indicative of fetal heart rate. By contrast, the pulse packet 44 includes three crossings 60 of the zero value of the amplitude axis where the Doppler ultrasound signal crosses from negative to positive, or alternatively three pulse peaks 61, which is at threshold of three crossings determined from clinical data analyses. Therefore, the electronic processor 22 determines that the hiccup pulse 44 is indicative of a hiccup.

In further embodiments, machine learning techniques can be used to classify portions of the spectrum of the Doppler ultrasound signal as indicative of hiccups or non-hiccups. In some embodiments, the frequency spectrum of the pulse packet is computed, e.g. using a Fast Fourier Transform (FFT) or the like, and the pulse packet (which is in the time domain) is combined with the computed frequency spectrum. Any pulse packet whose frequency spectrum meets a classification criterion is classified as a hiccup, and any pulse packet which does not meet the classification criterion is classified as a non-hiccup. For example, a classification criterion is selected that includes the frequency spectrum having one or more features selected from a group including: (1) a binary feature indicating whether the frequency spectrum has a higher-amplitude lobe at a lower frequency, a lower amplitude lobe at a higher frequency, and a valley separating the higher-amplitude lobe from the lower amplitude lobe; (2) the frequency of the peak of the frequency spectrum; and (3) the frequency spectrum having a higher-amplitude lobe at a lower frequency and a lower amplitude lobe at a higher frequency wherein the features include the center frequency of the lower amplitude lobe and the center frequency of the higher amplitude lobe. Advantageously, combining the pulse packet (e.g., in the time domain) with the computed frequency spectrum increases an accuracy of the detection of a hiccup.

Figure 4A:
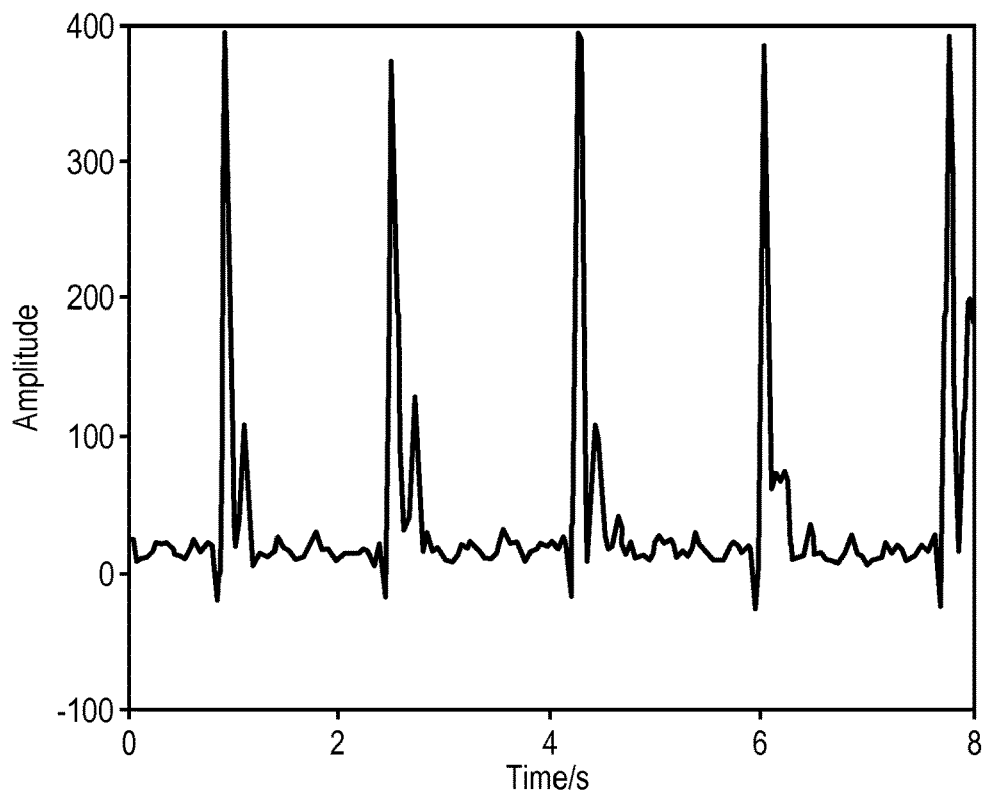
FIGS. 4A and 4B illustratively show the time domain signal of hiccups (FIG. 4A) and the corresponding power spectrum (FIG. 4B)
Figure 4B:
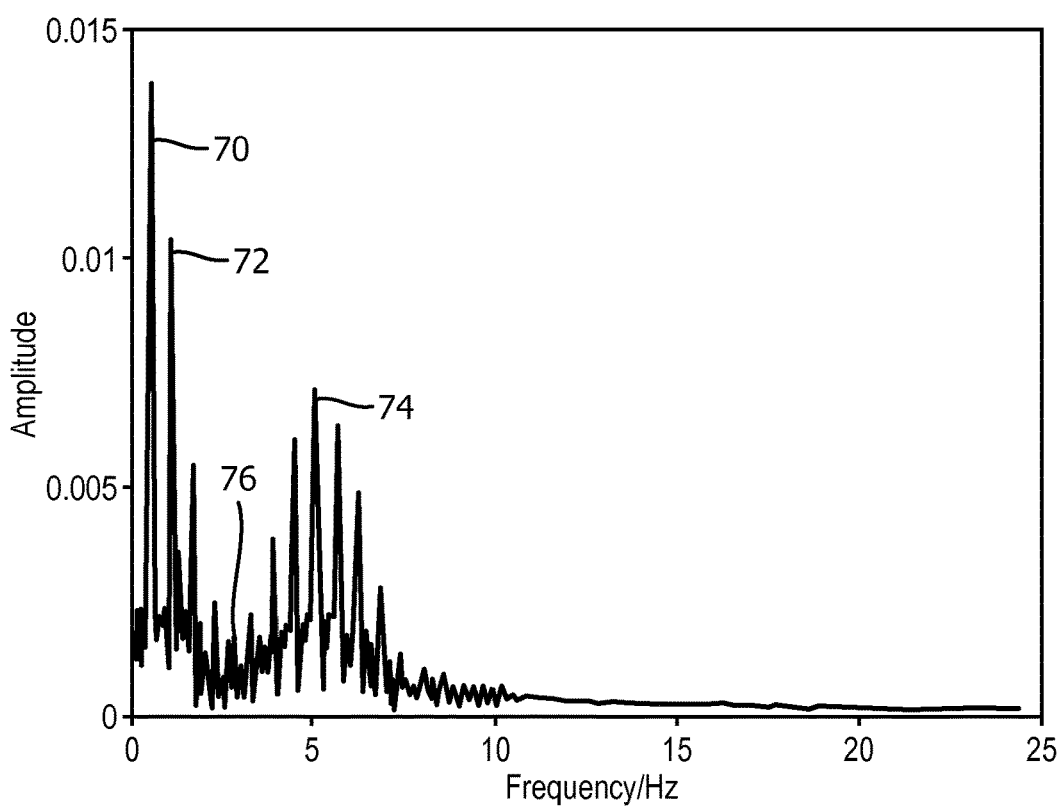
Figure 5:
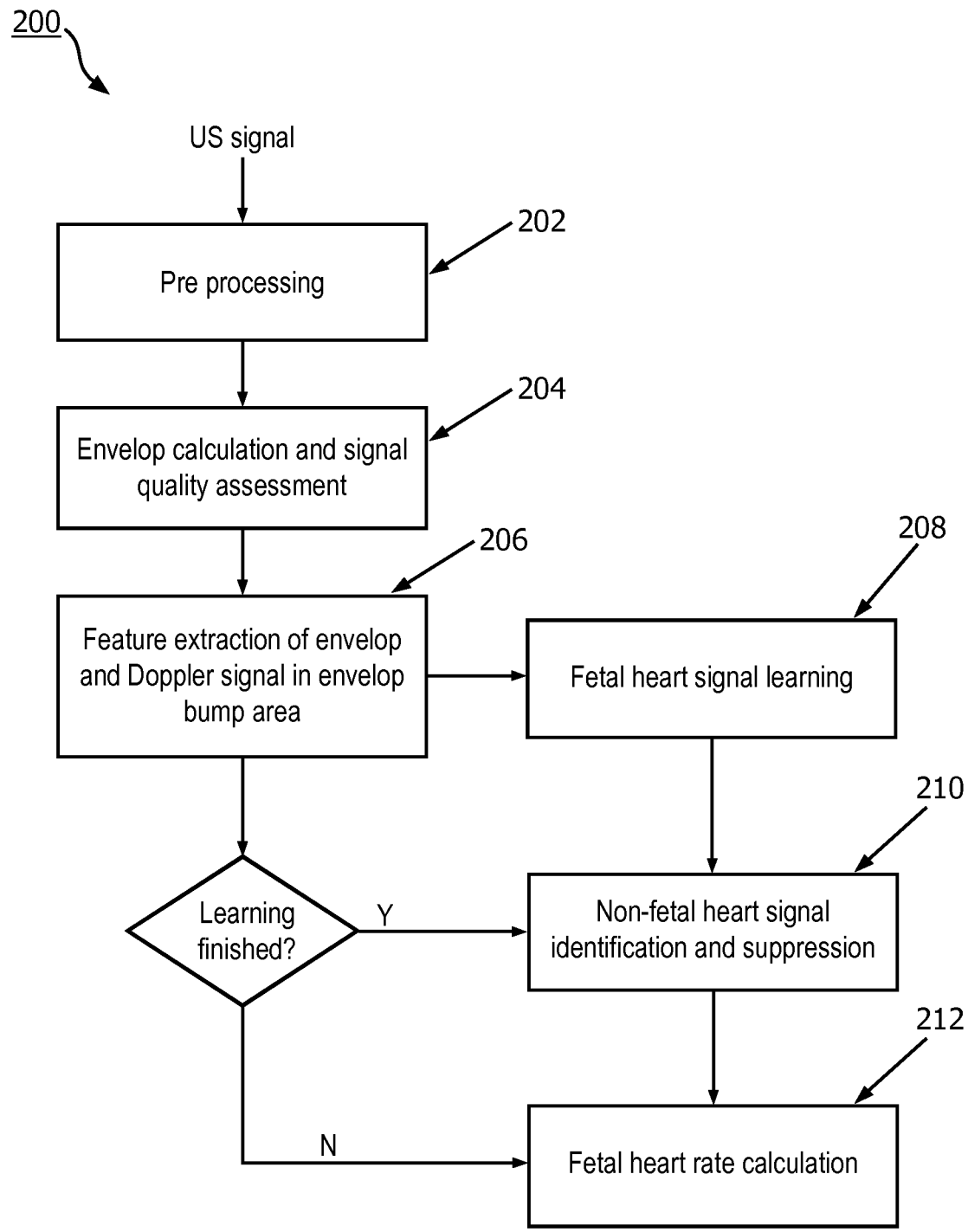
FIG. 5 shows another exemplary flow chart operation of the system of FIG. 1.

FIGS. 4A and 4B further illustrate these features. FIG. 4A shows a time domain signal of hiccups, while FIG. 4B shows a power spectrum with signals with fetal hiccups. In FIGS. 4A and 4B, the depicted signals show good periodicity both in the time frequency domains. Multiple harmonics exist in the frequency domain. The amplitude of these harmonics reduce gradually and then increase again to another level lower than dominant component. Once a pattern is determined from periodicity features or parameters, a hiccup is identified in the signal having. Several parameters can be identified in the spectrum. For example, there is a main frequency component 70, which is closest to y axis, a second harmonic frequency 72, which has second highest amplitude, a bump 74 including at least 2 harmonic frequencies, and is a minimum frequency 76 existing on the spectrum between the y axis and the bump. It will be appreciated that the hiccup classification step 106 may leverage both time domain features such as those described with reference to FIG. 3, and spectral features generated by machine learning as described with reference to FIGS. 4A and 4B, to provide improved discrimination to distinguish hiccups from fetal heartbeats. With reference to FIG. 5, a method or process 200 approach is described, in which the threshold for distinguishing pulse packets due to hiccups from pulse packets due to heart beats is determined by machine learning. At 202, a Doppler ultrasound signal of a fetus is acquired and filtered the Doppler ultrasound signal with a band pass filter to suppress a fetal movement component of the Doppler ultrasound signal. The band pass filtering operation removes motion data indicative of movement of the fetus not due to thoracic activity.

At 204, an envelope is calculated from the filtered signal. The envelope is used to determine a range of the amplitudes of peaks of the filtered signal. This operation occurs in real time. A signal quality of the signal is also determined to assess whether the signal should be discarded.

At 206, features are extracted from the envelope. For example, the number of peaks and zero-crossings are determined to determine activity (e.g., heart beat or hiccup) in the signal, and/or spectral features are extracted as described with reference to FIGS. 4A and 4B.

Referring back to FIG. 5, at 208, the extracted features are input into a machine-learning algorithm. The machine-learning algorithm is trained with training data which has already been determined as being indicative of a heart beat or a hiccup. The machine-learning algorithm can be continually updated as newly acquired data is obtained.

At 210, when the machine-learning process is finished, the portions of the signals determined to be caused by hiccups are identified and suppressed, thereby leaving only the portions of the signal indicative of heart rate.

At 212, when the machine-learning process is not completed, a fetal heart rate calculation is determined from the remaining portions of the signal that are not indicative of hiccups.

Figure 6:
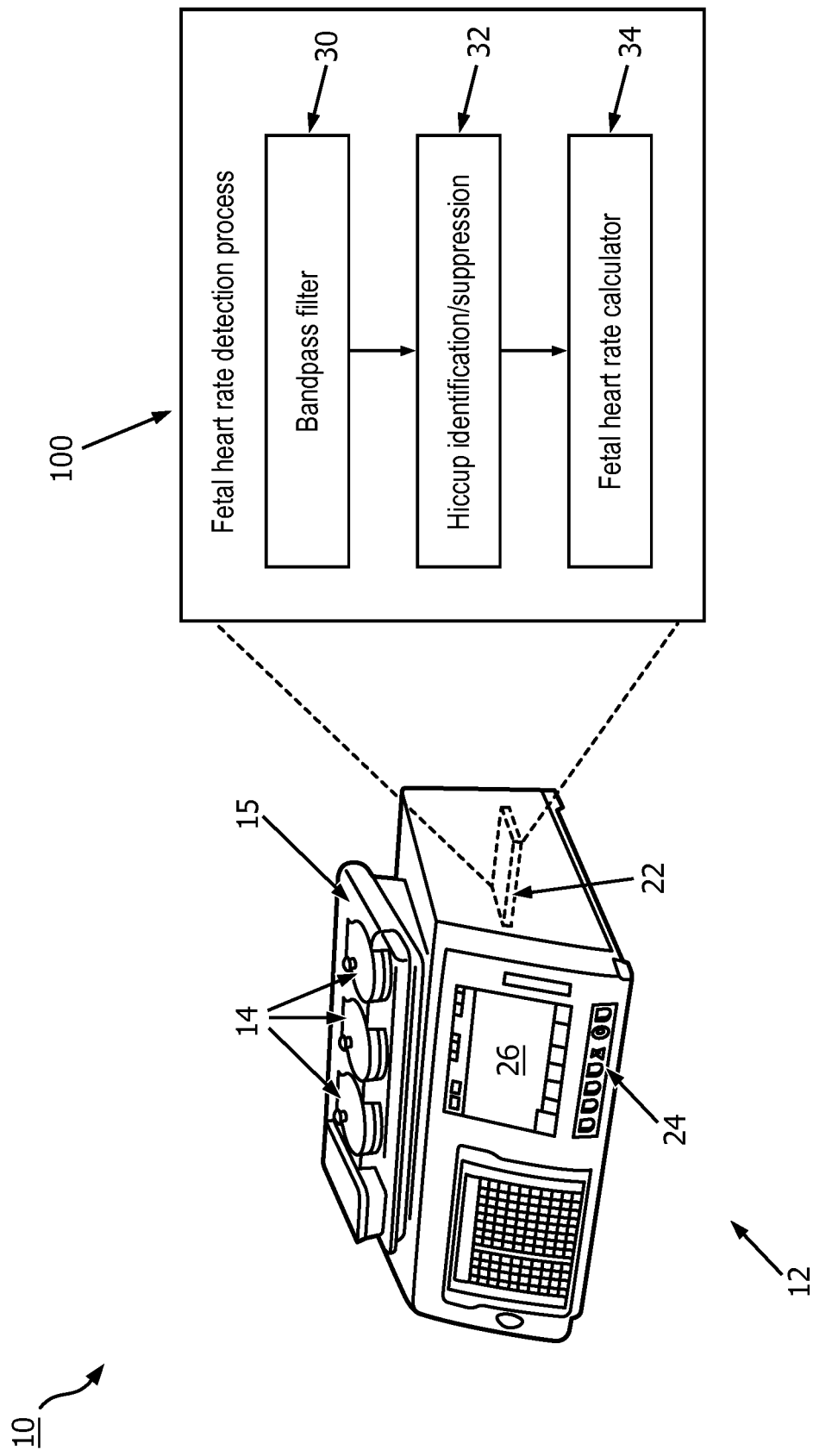
FIG. 6 diagrammatically shows a fetal heart rate detection system according to another aspect.

With reference to FIG. 6, an illustrative device or system 10 configured to detect a fetal heart rate is shown. As shown in FIG. 1, the device 10 includes a Doppler ultrasound device 12 including an ultrasonic transducer 14. (In the non-limiting illustrative example of FIG. 1, a set of three ultrasonic transducers 14 in a storage tray 15 is shown; the illustrative Doppler ultrasound device 12 may monitor one, two, or three mothers concurrently using these transducers). The ultrasonic transducer 14 is configured to acquire a Doppler ultrasound signal. For example, the ultrasound transducer 14 can be secured or otherwise attached to an abdominal area of a mother (not shown) carrying a fetus (not shown) such that the ultrasonic transducer 14 overlies a portion of the fetus (e.g., the fetus and the transducer are separated by the abdominal area of the mother).

The device 10 also includes at least one electronic processor 22, at least one user input device 24 such as an illustrative control panel with buttons, switches, soft keys, a full keyboard, and/or the like, and a display device 26. The illustrative electronic processor 22 is integral with the Doppler ultrasound device 12, but an otherwise-arranged electronic processor such as the electronic processor of a computer or the like (not shown) is additionally or alternatively contemplated. The illustrative display 26 is built into the Doppler ultrasound device 12, but in other embodiments, the display can be a separate component, e.g. a display of a computer or a standalone display monitor. The electronic processor 22 can be programmed to control the display device 26 to display the calculated heart rate signal.

The at least one electronic processor 22 is operatively connected with a non-transitory storage medium (not shown) that stores instructions which are readable and executable by the at least one electronic processor 22 to perform disclosed operations including performing a fetal heart rate detection method or process 100. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth. In some examples, the fetal movement detection method or process 100 may be performed by cloud processing.

The fetal heart rate detection process 100 typically includes a digitally implemented band pass filter 30 to remove fetal movement signals which are usually at lower frequency than the heartbeat pulse packets. As disclosed herein, the fetal heart rate detection process 100 further includes a hiccup identification and suppression component 32. A fetal heart rate calculator 34 computes the fetal heart rate with any pulse packets due to hiccups suppressed by the hiccup identification and suppression component 32.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

The invention claimed is:

1. A fetal movement detection method, comprising:
    identifying pulse packets in a Doppler ultrasound signal, each pulse packet comprising a pulse train of one or more pulses;
    classifying each of the identified pulse packets as a hiccup or non-hiccup based on at least one characteristic of the identified pulse packets;

suppressing the pulse packets of the Doppler ultrasound signal that are classified as a hiccup; and calculating a fetal heart rate from the Doppler ultrasound signal with the pulse packets classified as hiccups suppressed, wherein the classification operation further includes determining a pulse count comprising a number of crossings of the time axis or a number of pulse peaks for each of the pulse packets identified in the Doppler ultrasound signal and classifying any pulse packet whose determined pulse count is at or below a threshold as a hiccup.

2. The fetal movement detection method of claim 1, further comprising:

generating a statistical distribution of the pulse counts of the pulse packets identified in the Doppler ultrasound signal; and selecting the threshold based on the statistical distribution.

3. The fetal movement detection method of claim 1, wherein the classification operation further includes:

computing a frequency spectrum for each pulse packet; and classifying any pulse packet whose frequency spectrum meets a classification criterion as a hiccup.

4. The fetal movement detection method of claim 3, wherein the classification criterion includes the frequency spectrum having one or more features selected from a group including:

(1) a binary feature indicating whether the frequency spectrum has a higher-amplitude lobe at a lower frequency, a lower amplitude lobe at a higher frequency, and a valley separating the higher-amplitude lobe from the lower amplitude lobe;

(2) the frequency of the peak of the frequency spectrum; and (3) the frequency spectrum having a higher-amplitude lobe at a lower frequency and a lower amplitude lobe at a higher frequency wherein the features include the center frequency of the lower amplitude lobe and the center frequency of the higher amplitude lobe.

5. The fetal movement detection method of claim 1, further comprising, prior to performing the identifying, classifying, suppressing, and calculating operations, high-pass filtering the Doppler ultrasound signal to suppress a fetal movement component of the Doppler ultrasound signal.

6. A device configured to determine a fetal heart rate, the device comprising:

at least one electronic processor programmed to:

identify pulse packets in the Doppler ultrasound signal, each pulse packet comprising a pulse train of one or more pulses;

classify each of the identified pulse packets as a hiccup or non-hiccup based on at least one characteristic of the identified pulse packets;

suppress the pulse packets of the Doppler ultrasound signal classified as hiccups; and calculate a fetal heart rate from the Doppler ultrasound signal with the pulse packets classified as hiccups suppressed wherein the classification operation includes:

determining a pulse count comprising a number of crossings of the time axis or a number of pulse peaks for each of the pulse packets identified in the Doppler ultrasound signal; and classifying any pulse packet whose determined pulse count is at or below a threshold as a hiccup.

7. The device of claim 6, wherein the at least one electronic processor is further programmed to:

generate a statistical distribution of the pulse counts of the pulse packets identified in the Doppler ultrasound signal; and select the threshold based on the statistical distribution.

8. The device of claim 7, wherein the classify operation includes:

computing a frequency spectrum for each pulse packet; and classifying any pulse packet whose frequency spectrum meets a classification criterion to a hiccup.

9. The device of claim 8, wherein the classification criterion includes the frequency spectrum having one or more features selected from a group including:

(1) a binary feature indicating whether the frequency spectrum has a higher-amplitude lobe at a lower frequency, a lower amplitude lobe at a higher frequency, and a valley separating the higher-amplitude lobe from the lower amplitude lobe;

(2) the frequency of the peak of the frequency spectrum; and (3) the frequency spectrum having a higher-amplitude lobe at a lower frequency and a lower amplitude lobe at a higher frequency wherein the features include the center frequency of the lower amplitude lobe and the center frequency of the higher amplitude lobe.

10. The device of claim 6, wherein the at least one electronic processor is further programmed to:

prior to performing the identify, classify, suppress, and calculate operations, high-pass filtering the Doppler ultrasound signal to suppress a fetal movement component of the Doppler ultrasound signal.

11. The device of claim 6, wherein the calculating operation comprises:

calculating the fetal heart rate as a rate of occurrence of the identified pulse packets in the Doppler ultrasound signal with the pulse packets classified as hiccups suppressed.

12. The device of claim 6, wherein the at least one electronic processor is further programmed to:

suppress the pulses of the signal representative of a hiccup by attenuating the pulses by at least 3 dB.

13. A non-transitory computer readable medium having stored thereon program code readable and executable by one or more electronic processors to perform operations including:

identifying pulse packets in a Doppler ultrasound signal, each pulse packet comprising a pulse train of one or more pulses;

classifying each of the identified pulse packets as a hiccup or non-hiccup; based on at least one characteristic of the identified pulse packets;

suppressing the pulse packets of the Doppler ultrasound signal that are classified as a hiccup; and calculating a fetal heart rate from the Doppler ultrasound signal with the pulse packets classified as hiccups suppressed, wherein the classification operation further includes determining a pulse count comprising a number of crossings of the time axis or a number of pulse peaks for each of the pulse packets identified in the Doppler ultrasound signal and classifying any pulse packet whose determined pulse count is at or below a threshold as a hiccup.

* * * * *